(12) United States Patent
Preusche

(10) Patent No.: US 9,763,634 B2
(45) Date of Patent: Sep. 19, 2017

(54) PHASE-CONTRAST X-RAY IMAGING DEVICE

(71) Applicant: SIEMENS AKTIENGESELLSCHAFT, Munich (DE)

(72) Inventor: Oliver Preusche, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 29 days.

(21) Appl. No.: 14/893,171

(22) PCT Filed: May 22, 2014

(86) PCT No.: PCT/EP2014/060501
§ 371 (c)(1),
(2) Date: Nov. 23, 2015

(87) PCT Pub. No.: WO2014/187885
PCT Pub. Date: Nov. 27, 2014

(65) Prior Publication Data
US 2016/0066873 A1   Mar. 10, 2016

(30) Foreign Application Priority Data
May 22, 2013   (DE) .................. 10 2013 008 925

(51) Int. Cl.
*A61B 6/00* (2006.01)
*A61B 6/06* (2006.01)
*G21K 1/06* (2006.01)

(52) U.S. Cl.
CPC ............ *A61B 6/484* (2013.01); *A61B 6/4035* (2013.01); *A61B 6/4233* (2013.01);
(Continued)

(58) Field of Classification Search
CPC ..... A61B 6/484; A61B 6/4291; A61B 6/4035; G01N 23/20075; G01N 23/04; G21K 2201/067; G21K 1/067
See application file for complete search history.

(56) References Cited

U.S. PATENT DOCUMENTS 5,726,741 A * 3/1998 Kye .................. G03F 7/701
355/53
6,428,939 B1   8/2002 Yang et al.
(Continued)

FOREIGN PATENT DOCUMENTS

| WO | 2013004574 A1 | 1/2013 |
| WO | 2013160153 A1 | 10/2013 |
| WO | 2014180901 A1 | 11/2014 |

OTHER PUBLICATIONS

Pfeiffer et al., "X-ray phase contrast imaging using a grating interferometer", Europhysics News, vol. 37, No. 5, pp. 13-15, 2006.
(Continued)

*Primary Examiner* — Hoon Song
(74) *Attorney, Agent, or Firm* — Laurence Greenberg; Werner Stemer; Ralph Locher

(57) ABSTRACT

A phase-contrast x-ray imaging device is particularly suited for the medical field. The device includes an x-ray source for generating an x-radiation field and an x-ray detector having a one-dimensional or two-dimensional arrangement of pixels. A phase-contrast differential amplifier is positioned between the x-ray source and the x-ray detector. The phase-contrast differential amplifier amplifies spatial phase differences in the x-radiation field during operation.

13 Claims, 6 Drawing Sheets

(52) U.S. Cl.
CPC .............. *A61B 6/4291* (2013.01); *A61B 6/06* (2013.01); *G21K 1/065* (2013.01); *G21K 2207/005* (2013.01)

(56) References Cited

U.S. PATENT DOCUMENTS

| | | | |
|---|---|---|---|
| 2012/0041679 A1 | 2/2012 | Stampanoni et al. | |
| 2014/0146945 A1* | 5/2014 | Fredenberg | A61B 6/4233 378/62 |
| 2014/0252240 A1* | 9/2014 | Baker | G01N 23/005 250/370.05 |
| 2015/0055744 A1 | 2/2015 | Anton et al. | |

OTHER PUBLICATIONS

Zhou S. A. et al., "Development of phase-contrast X-ray imaging techniques and potential medical applications"; Physica Medica, ACTA Medica Edizioni e Congressi, Rom, vol. 24, No. 3, pp. 129-148, ISSN: 1120-1797, DOI: 10.1016/J.EJMP.2008.05.006, XP024341442, 2008.

Engel J., "Contrast-to-noise in X-ray differential phase contrast imaging," Nuclear Instruments and Methods in Physics Research, Sec. A 648, 2011, pp. 202-207, 2011.

Raupach et al., "Analytical evaluation of the signal and noise propagation in x-ray differential phase-contrast computed tomography", in: Phys. Med. Biol., 2011, vol. 56, pp. 2219-2244, DOI:10.1088/0031-9155/56/7/020.

Yaroshenko et al., "Non-binary phase gratings for xray imaging with a compact Talbot interferometer", Optics Express 22, 2014, DOI:10.1364/OE.22.000547, pp. 547-556, 2014.

Pfeiffer et al., "Phase retrieval and differential phase-contrast imaging with low-brilliance X-ray sources"; Nature Physics; vol. 2, Apr. 2006, pp. 258-261, doi: 10.1038/nphys265, 2006.

Bartl et al., "Grating-based high energy X-ray interferometry with the Medipix-detector in simulation and measurement", Journal of Instrumentation (JINST) 5, 10008, pp. 17, 2010.

Weber et al., "Noise in x-ray grating-based phase-contrast imaging", Med. Phys. 38 (7), Am. Assoc. Phys. Med., pp. 4133-4140, 2011.

Weitkamp et al., "X-ray phase imaging with a grating interferometer", Optics Express, vol. 13, No. 16, published Aug. 8, 2005, pp. 6296-6304, 2005.

Benner B., "Imaging with Parabolic Refractive X-Ray Lenses", Dissertation, RWTH Aachen, urn:nbn:de:hbz:82-opus-11521, pp. 1-140, 2005.

Momose A., "Recent Advances in X-ray Phase Imaging", Japanese Journal of Applied Physics, vol. 44, No. 9A, pp. 6355-6367, 2005.

Donath T. et al., "Phase-contrast imaging and tomography at 60 keV using a conventional x-ray tube source", Review of Scientific Instruments 80, 053701, 2009.

Cederström B., "A Multi-Prism Lens for Hard X-Rays", Dissertation, KTH Stockholm, pp. 1-135; 2002.

"X-ray phase imaging with a grating interferometer", T. Weitkamp at al., Aug. 8, 2005/vol. 13, No. 16/Optics Express.

Zhou, S.A., "Development of phase-contrast X-ray imaging techniques and potential medical applications", Physica Medica, Sep. 1, 2008, pp. 129-148 Acta Medica Edizioni e Congressi, Rome IT —ISSN 1120-1797, vol. 24, No. 3.

* cited by examiner

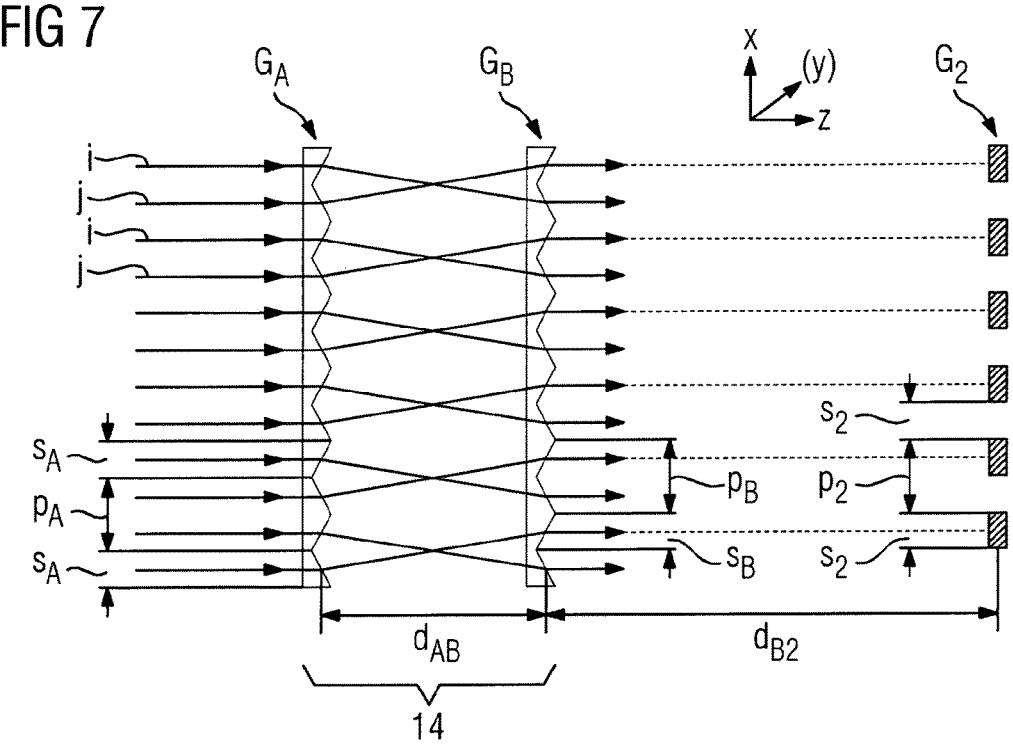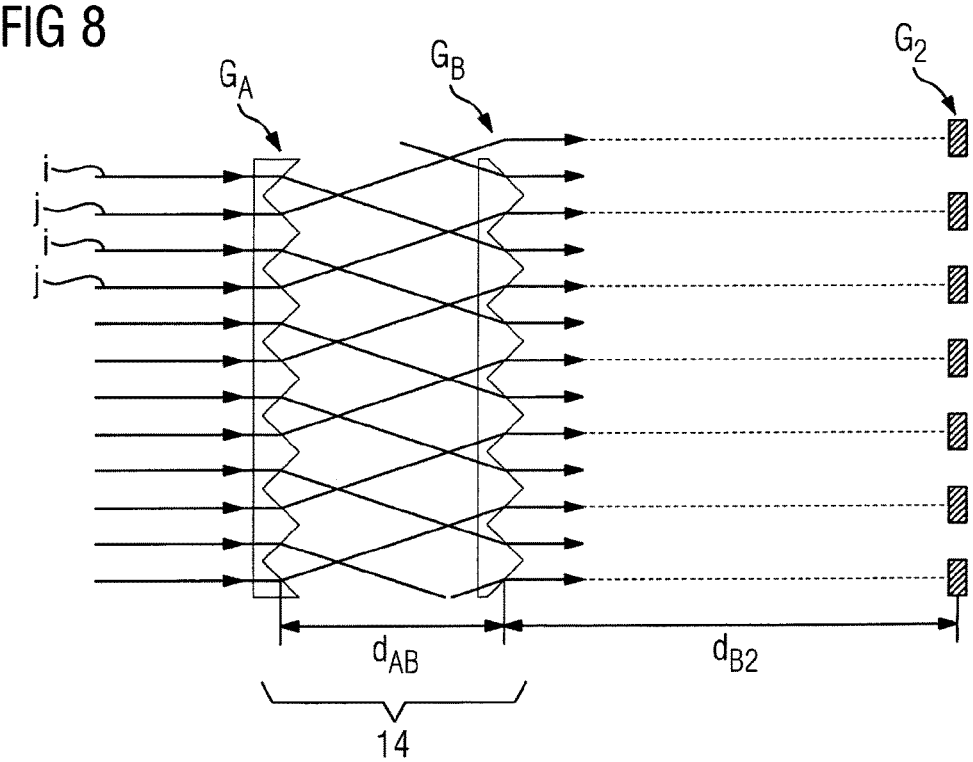

PHASE-CONTRAST X-RAY IMAGING DEVICE

BACKGROUND OF THE INVENTION

Field of the Invention

The invention relates to a phase-contrast x-ray imaging device, i.e. to an x-ray device for phase-contrast imaging, in particular for phase-contrast imaging in the medical field, comprising an x-ray source for generating an x-radiation field and an x-ray detector having a one-dimensional or two-dimensional arrangement of pixels.

The interaction of electromagnetic radiation in general, and x-radiation in particular, with a medium is typically described by specification of a complex refractive index. Real and imaginary part of the refractive index are in this case each dependent on the material composition of the medium to which the complex refractive index is assigned. Whereas the imaginary part indicates the absorption of the electromagnetic radiation in the medium, the real part of the refractive index describes the material-dependent phase velocity, and consequently the refraction of the electromagnetic radiation.

The majority of x-ray imaging devices currently in use serve exclusively for visualizing an absorption contrast and accordingly detect the material-dependent radiation absorption in an object that is to be examined, the intensity of the x-radiation transmitted through the object being recorded in a spatially resolved manner.

Still less widespread at the present time is the utilization of the refraction caused by the object and the associated material-dependent phase shift for the purpose of visualizing a phase contrast for the imaging. However, corresponding methods and devices are already undergoing development.

A Talbot-Lau interferometer, as described for example in "X-ray phase imaging with a grating interferometer", T. Weitkamp at al., Aug. 8, 2005/Vol. 13, No. 16/OPTICS EXPRESS, is typically used in this case for recording the phase shift by means of measurement instruments.

In a conventional Talbot-Lau interferometer, an x-ray source, a coherence grating $G_0$, a phase grating (or diffraction grating) $G_1$, an analysis grating (or absorption grating) $G_2$ and an x-ray detector constructed from a plurality of pixels are arranged along an optical axis. In this arrangement the coherence grating $G_0$ serves to ensure an adequate spatial coherence of the x-ray source. Accordingly, the coherence grating $G_0$ can be omitted in the case of an approximately punctiform x-ray source. An interference pattern, the intensity distribution of which is detected by means of the x-ray detector, is generated with the aid of the phase grating $G_1$, which typically has a uniform strip-like structure.

The period of said interference pattern is in this case typically significantly smaller than the size of the pixels of the x-ray detector, so a direct recording of the interference pattern by means of the x-ray detector is not possible. In order to be able nonetheless to measure the interference pattern, the analysis grating (or absorption grating) $G_2$, with the aid of which the interference pattern can be sampled by means of a spatial-periodic masking of x-radiation, is usually connected upstream of the x-ray detector. To that end the analysis grating $G_2$ is shifted in a plane perpendicular to the optical axis and the structure of the interference pattern. Alternatively to the analysis grating $G_2$, the coherence grating $G_0$ or the phase grating $G_1$ can also be shifted.

For the phase-contrast imaging, the object that is to be examined is positioned between the x-ray source (and the possibly present coherence grating) on the one side and the phase grating $G_1$ on the other side. Alternatively hereto, the object can also be positioned between the phase grating $G_1$ and the analysis grating $G_2$. In both cases the object causes the x-radiation to undergo a phase shift varying as a function of location or a change in direction of the wavefronts of the x-radiation which changes the interference pattern generated by the phase grating $G_1$, i.e. the intensity distribution of the x-radiation, in a measurable manner. The changed interference pattern is then detected in the above-described way by means of the x-ray detector and finally the location-dependent phase shift is inferred by back-calculation from the measured intensity distribution of the interference pattern, the image information being obtained immediately directly from the phase or from the phase shift. Alternatively, the image information can also be determined from the density (i.e. the integrated phase) or the angular spread (dark field). Furthermore, the phase-contrast image is sometimes calculated with a simultaneously acquired absorption contrast image in order to reduce the image noise.

The desired advantage of phase-contrast x-ray imaging in this case consists in the fact that structures in the so-called soft tissue (in particular tissue, water and body fat) are generally delineated from one another more sharply in the phase contrast mode than in the absorption contrast mode. In this case the resolution capacity of a corresponding phase-contrast x-ray imaging device is substantially determined by the characteristics of the Talbot-Lau interferometer used, and in particular by its geometric dimensions. In this case the resolution capacity or sensitivity can be increased for example by having recourse to a higher Talbot order and accordingly increasing the distance between the phase grating and the analysis grating for example by the factor 3. However, the dimensions of the entire structure will be increased as a result and in addition the usable bandwidth of the spectrum of the electromagnetic radiation will be limited. Alternatively or in addition hereto, the resolution capacity can also be increased through the use of gratings having finer structures, although in this case there exists the problem that the production of finer structures is associated with a greater technical complexity.

BRIEF SUMMARY OF THE INVENTION

Proceeding from this starting point, the object underlying the invention is to improve phase-contrast x-ray imaging.

This object is achieved according to the invention by means of a phase-contrast x-ray imaging device having the features of claim 1. Advantageous embodiment variants and developments of the invention, some of which are inventive when considered per se, are set forth in the dependent claims and the following description.

A corresponding phase-contrast x-ray imaging device is in this case designed in particular for the medical field and comprises an x-ray source for generating an x-radiation field and an x-ray detector having a one-dimensional or two-dimensional arrangement of pixels. In this configuration a phase-contrast differential amplifier is positioned between the x-ray source and the x-ray detector and with its aid spatial phase differences in the x-radiation field are amplified during operation.

Thus, in particular local phase shifts induced by an examination object are selectively amplified such that as a result more conspicuous changes occur in an interference pattern which tend to be more easily recordable by means of measurement instruments. In this way a structure is then realized in which the sensitivity is increased in comparison with a conventional Talbot-Lau interferometer without the grating period of a grating used having been shortened for this purpose, and without the overall installation length having been increased. The sensitivity is therefore effectively decoupled from the purely geometric proportions.

A narrowband x-ray source is expediently employed here as an x-ray source, i.e. for example an x-ray tube having a downstream-connected filter which allows x-radiation to pass in a very narrow frequency band, or else a synchrotron radiation source, in particular laser-driven, such as the compact CXS, for example. In this case it is possible in principle to use different energies of hard x-radiation and accordingly an x-radiation energy matched to the particular purpose is expediently applied (e.g. anode voltage of the x-ray tube 25 kVp for mammography or 100 kVp for computed tomography).

Basically, this structure, and in particular the phase-contrast differential amplifier, or at least the principle behind it, can also be applied to applications having wavelengths adjacent to visible light or electromagnetic radiation (IR, UV) and be used for example for a Shack-Hartmann sensor.

Furthermore, the phase-contrast differential amplifier is preferably embodied in such a way that unaffected x-radiation, that is to say in particular x-radiation which has not experienced a change in direction of the wavefront due to an object that is to be examined, experiences a uniform phase shift on account of the phase-contrast differential amplifier. The phase shift caused by the phase-contrast differential amplifier is therefore for example initially independent of the entry position of the unaffected x-radiation at the phase-contrast differential amplifier.

In addition, the interference pattern required for the interferometric measurement method is preferably also generated by means of the phase-contrast differential amplifier and accordingly the phase-contrast differential amplifier in this case replaces the phase grating $G_1$ of a conventional Talbot-Lau interferometer. The uniform phase shift effected by the phase-contrast differential amplifier then takes place as in the case of a phase grating $G_1$ of a conventional Talbot-Lau interferometer. With the latter, a rectangular binary profile composed of ridges and intervening spaces is typically used in order to generate a strip-shaped interference pattern, the phase of the x-radiation being shifted by $\pi$ (or $\lambda/2$) at the ridges ("PI grating").

In this case it is further of advantage if the phase-contrast differential amplifier comprises two diffraction gratings which, when viewed in a radiation incidence direction, are arranged one behind the other, the phase-contrast differential amplifier preferably having two identical diffraction gratings and in particular being constructed from precisely two diffraction gratings. Accordingly, the phase grating $G_1$ of a conventional Talbot-Lau interferometer is replaced, according to an advantageous embodiment, by two identical diffraction gratings, with the aid of which on the one hand the interference pattern is generated and with the aid of which in addition local phase differences induced by an examination object are amplified. The idea to replace the element generating, refracting or diffracting the interference pattern in a Talbot-Lau interferometer, in other words the phase grating $G_1$, by two light-diffracting elements, i.e. two diffraction gratings $G_A$ and $G_B$, is based on the considerations set forth hereinbelow.

With the conventional Talbot-Lau interferometer, changes in direction of the wavefronts of electromagnetic radiation, i.e. effectively phase gradients, are detected on the basis of microscopically small changes in intensity. In this case a strip-shaped interference pattern is generated by means of the phase grating $G_1$ in that each ridge of the phase grating $G_1$ shifts the phase of the incident x-radiation typically by half a wavelength (alternatively a shift by a quarter of a wavelength is performed). As a result, an interference pattern made up of narrow strips can be detected at a specific (uneven) multiple of the so-called "Talbot" distance behind the phase grating $G_1$, the analysis grating $G_1$ then being positioned at this position.

In a simplified consideration the intensity pattern behaves in this case in the manner of a shadow generated by the phase grating $G_1$. Given a corresponding alignment of the analysis grating $G_2$ relative to the strip-shaped intensity pattern, a maximum or minimum intensity $I_{max}$ or $I_{min}$, respectively, will pass through the analysis grating $G_2$, the phases $\Phi=0$ or $\Phi \pm 1$ n in turn being inferred from the intensity measured by means of the x-ray detector using measurement instruments.

The typically additionally used coherence grating or absorption grating $G_0$ serves in this case simply to compensate for the effects of the extension of the x-ray source, in most cases an x-ray tube. Said grating is placed directly on the x-ray tube and ensures that each of its slits as radiation source projects the same strip pattern onto the analysis grating $G_2$ (without $G_0$ many strip patterns would overlap and bring about a uniform intensity at $G_2$). The absorption grating $G_0$ can be omitted when an x-ray source is used which to a very good approximation generates plane waves (synchrotron), or in the case of x-ray sources which to a good approximation can be regarded as punctiform sources (microfocus).

As the phase-contrast imaging device is provided in particular for application in the medical field, it is furthermore of particular significance how the absorption of the x-radiation by the analysis grating G2 affects the required x-ray dose.

In this arrangement the transmission T behind an object that is to be examined, i.e. in particular behind a patient, is determined by the intensity ratio $T=I/I_0$, where $I_0$ is the average intensity without $G_1$ and $G_2$. The noise (represented by the standard deviation $\sigma_\phi$) is in this case proportional to $(\Delta t\, I_0)^{-2}$ (as in Monte Carlo simulations), i.e. in order to halve the noise, four times the dose $\Delta t\, I_0$ is required.

In the case of differential phase contrast (and also in the case of dark field acquisitions) a proportional dependence of the noise $\sigma_\phi$ on the strip phase $\phi$ results:

$$\sigma_\phi^2 \propto 1/(\Delta t I_0 V^2 T)$$

In this case V is the (strip) visibility, where:

$$V=(I_{max}-I_{min})/(I_{max}-I_{min})$$

The variables $I_{max}$ and $I_{min}$ in this case denote the maximum and minimum intensities as a function of the x position of a shiftable $G_0$, where visibility V and the transmission T can in each case vary within the limits 0-100%.

In order to keep the noise at a specific value, $\Delta t\, I_0\, V^2\, T$ must therefore remain unchanged. An efficiency $\eta$ of the optics behind the patient can be defined as:

$$\eta_\phi = V^2 T$$

An object of the present application is to optimize $\eta_\phi$, i.e. to achieve a dose minimization for a given $\sigma_\phi$ (in contradistinction to $\sigma_{\Phi'}$ or $\sigma_\Phi$), where $\Phi$ denotes the phase of the actual wavefront and $\Phi'$ its spatial change $\Phi'=\partial\Phi/\partial x$. In this case $\Phi'$ is given by:

$$\Phi'=\partial\Phi/\partial x=\phi p_2/(\lambda d_{12})$$

where $p_2$ is the grating period of $G_2$, which corresponds to double the ridge width $s_2$ of the grating, and where $d_{12}$ is the distance between the gratings $G_1$ and $G_2$.

With the definition of the sensitivity S as $S=d_{12}/p_2$, the following applies for a given design wavelength $\lambda=\lambda_D$:

$$\sigma_{\Phi'} \propto \sigma_\psi/S$$

Thus, the higher the sensitivity, the lower is the noise. From:

$$\sigma_{\Phi'}^2 \propto \sigma_\phi^2/S^2 \propto 1/(\Delta t I_0 S^2 V^2 T)$$

it follows as above for a predefined noise $\sigma_{\Phi'}$ that the dose $\Delta t \cdot I_0$ is proportional with $\eta_{\Phi'}$, where:

$$\eta=\eta_{\Phi'}=S^2 V^2$$

where $\eta=\eta_{\Phi'}$ is the efficiency of the measurement behind the patient.

In existing prior art implementations $\eta$ is typically too small, in particular in the case of high photon energies (e.g.: 100 kVp tube voltage and correspondingly, for example, 65 keV design energy or 19 pm design wavelength of the photons), thus usually resulting in the past for phase-contrast images in a higher radiation exposure for a patient than in the case of absorption imaging. In this case a low visibility V is indicated as reason in the specialist literature.

Since, however, very many measured values turn out to be relatively small, an increase in the sensitivity of the structure would also compensate for a lower visibility for the majority of the measured values. If measured values nonetheless need to be acquired, which as a result are excluded from the measurement range, there exists in principle the possibility, within the scope of a subsequent measurement with lower sensitivity and significantly smaller radiation dose (i.e. high noise), to identify these points and to correct the corresponding measured values (even at the expense of higher noise).

As explained hereintofore, the sensitivity of the structure is in this case proportional to the grating period $p_2$ or else proportional to the root of the grating distance $d_{12}$. In particular, however, it is not desired here to increase the distance between the two gratings $G_1$ and $G_2$, i.e. $d_{12}$, arbitrarily. It would be more favorable to realize a higher sensitivity, without significantly reducing the grating periods, since this reduces the visibility in particular at high photon energies. (At lower photon energies, e.g. 30 keV, it is possible on the other hand simply to resort to a higher Talbot order. Thus, the distance $d_{12}$ is increased for example by the factor 3 and once again a visible interference pattern having higher sensitivity is obtained.) This therefore raises the question as to what other possibilities there are for increasing the sensitivity further.

If a conventional Talbot-Lau interferometer is now considered, this is used ultimately to determine the angle of the incident light or of the x-radiation, in other words the direction of the wavefronts. If, for example, the phase grating $G_1$ is now rotated through a small angle around a y-axis which extends through the center point of $G_1$ and is parallel to the ridges of $G_1$, nothing changes in principle in terms of the position of the interference pattern, since the rotation has practically no effect on the visible period and the deviations on a z-axis along which the gratings of the Talbot-Lau interferometer are arranged have no relevance because lengths along the z-axis are greater by a multiple than the grating periods along a x-direction which is perpendicular to the y-axis on the one hand and to the z-axis on the other.

If in this situation the x-ray source is now rotated together with $G_0$ and $G_1$ such that $G_1$ once again assumes the original position, there is a change in the alignment of the interference pattern with respect to $G_2$, which was not moved at the same time, and moreover exactly corresponding to the rotation of the incident radiation, i.e. the rotation of the x-ray source together with $G_0$ about the center point of $G_1$. This means that the alignment between the interference pattern and $G_2$ exactly reflects the direction of the radiation incident in $G_1$, precisely as though the interference pattern were simply a shadow cast by $G_1$ and everything happens purely geometrically.

In this case a rectangular binary profile is typically used for the phase grating $G_1$, in which profile quasi strip-shaped ridges and strip-shaped free spaces are arranged next to one another in alternation, the phase of the electromagnetic radiation being shifted by $\pi$ or $\lambda/2$ at the ridges. In this case an illumination by means of plane waves is generally assumed and accordingly the following applies to the distance $d_{12\|}$ between the phase grating $G_1$ and the analysis grating $G_2$:

$$d_{12\|}=p_1^2/(8\lambda)$$

In the case of an incoherent source having spherical propagation (x-ray tube), on the other hand, the distance changes in accordance with the lens equation:

$$1/f=1/g+1/b$$

where the focal distance $f=d_{12\|}$, the object distance $g=d_{01}$ and the image distance $b=d_{12}$ (since path length differences are indirectly proportional to distances along the optical axis and since the lens equation reflects said indirect proportionality).

Alternatively, higher uneven Talbot distances, such as three times, five times or seven times, for example, can also be used for the positioning of the analysis grating $G_2$ (this, however, shortens the grating periods, insofar as the installation length $d_{12}$ is retained, for which reason it is usually disregarded at higher photon energies).

In the following, however, a phase grating $G_1$ is considered which shifts the phase by $\pi/2$ or $\lambda/4$ ("PI half-pitch grating") and possesses half the period of the above-cited PI grating. Since $d_{12\|}=p_1^2/(2\lambda)$ applies in this case, a "PI grating" can be directly exchanged for "PI half-pitch gratings" (of half the period) in a structure, without the distances along the optical axis or the grating periods ($p_0$ or $p_2$) having to be adjusted.

Although this also applies to higher uneven Talbot distances, when electromagnetic radiation having too wide a frequency spectrum is used the "PI half-pitch grating" possesses the unpleasant characteristic that, depending on wavelength, some of the interference strip patterns are shifted by half a period, thereby reducing the visibility. This is another reason why no higher Talbot distances are used in the following consideration.

It is now apparent that maximum visibility is given in the case of a "PI half-pitch grating" $G_1$ when the latter shifts electromagnetic radiation of a design wavelength $\lambda_D$ by precisely one quarter of the wavelength (or 90°). If, on the other hand, a smaller shift takes place (e.g. only by $f^* \lambda/4$ where $f^*$ is from the range [−100%, +100%]), then the visibility of the interference pattern is reduced sinusoidally, which is to say that the visibility drops to about $\sin(f^* \pi/2)$ of the original visibility. In particular at small values of $f^*$, the contrast is therefore virtually linear to $f^*$, a negative contrast also being possible, which is to say that areas of higher and lower intensity in the strip pattern change positions (with a "PI half-pitch grating" the path length differences between a direct beam through two corresponding strip centers and one through an adjacent strip center amount to a quarter of the design wavelength. This means that a quarter wavelength (i.e. $\pi/2$) of phase deviation is sufficient in order to compensate for the path length differences in one case and to achieve extinction in the other case. This situation is symmetrical: if, for example, a phase deviation of PI half-pitch is now incorporated in the case of unevenly numbered strips instead of in the case of strips formerly having even numbering, the differences now compensate one another there at $G_2$, where they had previously extinguished one another, and vice versa).

Proceeding from these considerations, a new approach is now pursued according to which the angle of the incident electromagnetic radiation or the direction of the wavefronts, represented by the slope $\Phi'=\partial\Phi/\partial x$ of the phase $\Phi$ of the incident electromagnetic radiation is as it were translated into a periodic rectangular phase deviation of magnitude $f^* \lambda/4$, such that $f^* \sim \Phi'$, where the visibility of the interference pattern for $f^*$ or $\Phi'$ is then proportional to $f^*$ or $\Phi'$. In this case the measurement of the visibility permits the slope of the phase to be determined, and consequently the direction of the wavefronts.

If the incident electromagnetic radiation is then scattered over a certain small angular range, the contrast values for the individual angles mutually average one another. That is to say that the dark field signal no longer has to be visible, though seen positively it also does not interfere with the measurement of the phase via the visibility. If, however, the scatter angle range increases, it will of course reduce the visibility at some point in time.

If the sensitivity is high, with $f^*$ changing strongly with $\Phi'$, then the position of the strips of the interference pattern will practically not change at small $\Phi'$, and a measurement of the contrast is sufficient $(I_2-I_1)/(I_2+I_1)$ (e.g. two intensity measurements $I_1$ and $I_2$, where $G_2$ is shifted by half a period $s_2=p_2$ between the two measurements).

In the case of the phase-contrast differential amplifier being used in a computed tomography system, the method from application US 2012/0041679 A1 could be applied in this connection. It is described therein that after a half revolution of the gantry of the computed tomography system the deflection of the light has the reverse sign, as well as also the contrast in the case of the above-described measurement method, such that the brighter and darker areas are interchanged for one another. This would render a displacement of any gratings unnecessary.

The desired translation of the slope of the phase into a corresponding phase deviation is now realized with the aid of two diffraction gratings $G_A$ and $G_B$, which then replace the phase grating $G_1$ of a conventional Talbot-Lau interferometer. The two diffraction gratings $G_A$ and $G_B$ are in this case preferably embodied in a similar vein and implemented in the manner of a lens grating $G_L$, as is described in WO 2013/160 153 A1. Strictly speaking, the diffraction gratings $G_A$ and $G_B$ represent a simple limiting case of the lens grating $G_L$. Insofar as no differing description is given in the following, the entire contents and disclosure of said prior application are also part of the present invention.

A diffraction grating $G_A$ and/or $G_B$ according to the invention in this case has, exactly like a lens grating $G_L$, a transverse surface which is spanned by an x-axis and a y-axis perpendicular thereto, and which is to be aligned substantially (i.e. exactly or at least approximately) at right angles to a radiation incidence direction. The provided radiation incidence direction in this case defines a z-axis of the diffraction grating which, in the provided installation position of the diffraction grating, is aligned in particular parallel to an optical axis of the x-ray imaging device. The transverse surface can in this case be defined within the spatial volume occupied by the diffraction grating essentially at any z position (i.e. position along the z-axis). It is assumed simply by way of example in the following that the transverse surface is formed by the "front" end face of the diffraction grating via which the radiation is incident in the diffraction grating.

The axes introduced hereinabove span a Cartesian coordinate system. The spatial directions defined by the orientation of the x-, y- and z-axis are in this case designated hereinbelow as the (positive) x-, y- and z-direction, respectively. The opposite spatial directions in each case are designated as the (negative) x-, y- and z-direction, respectively. Positions on the x-, y- and z-axis are designated as x, y and z positions, respectively.

According to the desired property of the lens grating $G_L$ to diffract adjacent heterogeneous structures of the interference pattern into different focuses (i.e. focal points or focal lines), the transverse surface of a lens grating $G_L$ is subdivided into diffraction strips, in each case elongated in the y-direction, which are arranged next to one another in parallel rows in the x-direction. Adjacent diffraction strips are different from one another in this case in that they are always aligned to different focuses in terms of the diffraction properties of the grating material arranged in each case in the vicinity of said diffraction strip. In other words, the material of the lens grating $G_L$ which is arranged along the z-axis above and/or below a diffraction strip is embodied in such a way that it diffracts radiation at least of a specific design wavelength into a specific focus, whereas the material of the lens grating $G_L$ which is arranged along the z-axis above and/or below an adjacent diffraction strip diffracts the radiation into a different focus. In this case the transverse surface and the diffraction strips formed thereon are mathematical abstract structures.

The radiation-diffracting effect of the lens grating $G_L$ is generated by means of a plurality of diffraction ridges made of an optically comparatively thin base material (i.e. a solid material having a comparatively low real part of the refractive index for x-rays), said diffraction ridges being arranged in alternation with optically comparatively dense interspaces. Due to the separating interspaces the diffraction ridges extend within the transverse surface necessarily at least approximately parallel. In this arrangement the diffraction ridges are preferably formed from gold, nickel or silicon. The interspaces are formed optionally by (air- or liquid-filled) gaps or by intermediate ridges made of an optically comparatively dense material (i.e. a solid material having a comparatively large real part of the refractive index for x-rays), e.g. made of photoresist. It should be taken into account in this case that for x-rays the real part of the refractive index in all materials is less than one, so that for x-rays—unlike for visible light—solid materials always represent the optically thinner medium in comparison with a vacuum or air.

The surface areas occupied in each case by the diffraction ridges within the transverse surface are in this case typically not congruent with the diffraction strips, which are defined only by the radiation-diffracting properties of the diffraction grating.

According to an embodiment alternative not described in WO 2013/160 153 A1, the diffraction ridges of the lens grating $G_L$ are for example embodied in such a way that within the transverse surface they extend at least in sections diagonally (that is to say at an oblique angle, i.e. at an angle greater than 0° and less than 90° to the y-axis). The at least section-wise diagonal course of the diffraction ridges in the transverse surface is in this case characterized in that for at least one diffraction ridge the lateral faces delimiting said diffraction ridge in the x-direction extend within the transverse surface across at least two diffraction strips. Since, on account of the interspaces, the diffraction ridges must run at least approximately in parallel, this property necessarily extends to all of the diffraction ridges (with the exception of any diffraction ridges at the edges of the transverse surface whose lateral face can extend only over one diffraction strip on account of the edge position). Preferably the lateral faces of all of the diffraction ridges extend—apart from possible edge effects—regularly across a plurality of diffraction strips, in particular across all of the diffraction strips.

In a different, though in terms of content fully equivalent, formulation, the "diagonal course" of the diffraction ridges in the transverse surface is characterized in that at least one diffraction ridge extends across at least four diffraction strips. Owing to the at least approximately parallel course of the diffraction strips—apart from possible edge effects—this property, too, applies necessarily to all diffraction ridges.

By virtue of the above-described properties the "diagonal layout" of the diffraction ridges of the alternative embodiment of the lens grating $G_L$ is qualitatively different from the "strip-shaped layout" of the diffraction ridges of the lens grating $G_L$ disclosed in WO 2013/160 153 A1. There, the diffraction ridges extend in the longitudinal direction of the diffraction strips, i.e. in the y-direction. In that case the lateral faces of each diffraction ridge always remain in each case within the space allocated to a single diffraction strip, as a result of which the strip-shaped diffraction ridges can only extend across two or at most three diffraction strips.

As is already described in WO 2013/160 153 A1, the lens grating $G_L$ according to the invention can be used instead of the analysis grating $G_1$ of the traditional Talbot-Lau interferometer. In this case the lens grating $G_L$ is arranged at its focal distance from the x-ray detector such that the x-radiation is focused through the lens grating $G_L$ directly onto the individual pixels or pixel columns of the x-ray detector. Alternatively hereto, the lens grating $G_L$, as is likewise described already in WO 2013/160 153 A1, can be arranged between the phase grating and the analysis grating. In this case the x-radiation is focused through the diffraction grating onto the slits and ridges of the analysis grating.

On account of the property of the lens grating $G_L$ to diffract a plurality of adjacent structures corresponding to one another (e.g. intensity maxima or intensity minima) of the interference pattern in each case to a common focus, the lens grating $G_L$ acts as a periodic arrangement of positive lenses by means of which the interference pattern is coarsened. This enables use to be made of a correspondingly coarser analysis grating that provides better absorption in the grating ridges, thereby improving the visibility. This in turn enables the image noise and the x-ray dose to be reduced, in particular in the case of high-energy (shortwave) x-radiation. If the analysis grating is omitted in an alternative embodiment, the absorption caused thereby is absent, as a result of which a reduction in the image noise and the x-ray dose is likewise achieved, in particular in the case of low-energy (longwave) x-radiation.

Since a lens grating $G_L$ can generally be manufactured to a smaller installation height than an analysis grating, the strip width of the lens grating $G_L$ can be chosen smaller compared to the typical strip width of an analysis grating. As a result a greater distance (i.e. corresponding to a higher multiple of the Talbot distance) can be set between the phase grating and the lens grating $G_L$ than between the phase grating and the analysis grating of a standard Talbot-Lau interferometer. This results in a higher (angular) sensitivity, thereby outweighing the disadvantage of a somewhat lower visibility. This enables a further improvement with regard to the image noise and/or a further reduction in the x-ray dose.

As is already described in WO 2013/160 153 A1, the lens grating $G_L$ is preferably produced in a photolithographic production process, in particular using the so-called LIGA method (LIGA=Lithographie-Galvanik-Abformung= lithography, electroplating and molding) or by means of reactive ion etching.

A limiting factor for the production of the lens grating $G_L$ in this case is the aspect ratio constrained by production methods, which is determined at a given grating height in the z-direction by the manufacturable minimum distances between the sidewalls of the diffraction ridges, namely— according to the actual production method—by the minimum thickness of the diffraction ridges and/or the minimum thickness of the interspaces.

As is widely recognized, at a given grating height and with given diffraction properties of the diffraction strips, particularly great minimum distances between the sidewalls of the diffraction ridges—both within the diffraction ridges and between adjacent diffraction ridges—can be maintained as a result of the diagonal layout of the diffraction ridges. This in turn enables the manufacture of lens gratings $G_L$ having a particularly great grating height in the z-direction or a particularly small width of the diffraction strips. Such lens gratings $G_L$ enable the realization of phase-contrast x-ray imaging devices having a particularly short installation length and a particularly high sensitivity.

In a preferred embodiment the diffraction ridges are in each case formed in the manner of slanted prisms inclined in the y-direction, the base area and top area of which in each case lie in the end faces of the lens grating $G_L$ that run parallel to the transverse surface. In said embodiment the lens grating $G_L$ is produced in particular, as is already described per se in WO 2013/160 153 A1, by means of a photolithographic process, in particular LIGA, with off-axis illumination of the photoresist layer by means of exposure to x-radiation. The base area and the oppositely disposed top area of the prism each have in this case generally a complex polygonal shape. At the side edges of the lens grating $G_L$ the diffraction ridges—departing from a pure prism shape—can be cut off in order to form edge faces aligned in the z-direction. By means of the implementation of the diffraction ridges as slanted prisms inclined toward the transverse surface a comparatively strong diffraction is achieved without substantial degradation of other optical properties, in particular absorption and visibility.

The diffraction ridges are arranged in particular in such a way that a material structure repeating itself with a y period length in the y-direction results in each diffraction strip. The diffraction ridges are therefore fashioned in such a way that in each diffraction strip they always assume parallel-shifted, congruent and uniformly spaced-apart surface sections. In this case the diffraction ridges are inclined in the y-direction in such a way that the top area of each diffraction ridge opposite the base area is offset by a whole number of period lengths, in particular by precisely one period length, with respect to the base area. The two oppositely disposed end faces of the lens grating $G_L$ in the z-direction accordingly have an identical layout, i.e. an identical material structure formed from diffraction ridges and interspaces.

Preferably the lateral faces of the diffraction ridges are composed in each case of an alternating arrangement of active subareas having a comparatively strong diffraction effect in the x-direction and passive subareas having a small or vanishing diffraction effect in the x-direction. In this case the active subareas can be regarded as diffracting surfaces of (sub)prisms which, with their non-diffracting rear faces, are combined into a multi-prism forming the respective diffraction ridge.

The active and passive subareas are in this case preferably each formed by means of plane (uncurved) surface sections. The diffraction effect of each subarea is in this case determined by the associated gradient. Referred to as a gradient in this context is the slope $g=\Delta z/\Delta x$ which said subarea has in a section along an xz plane (i.e. a plane spanned by the x-axis and the z-axis). The greater the gradient g, i.e. the steeper the respective subarea is inclined toward the transverse surface, the stronger the incident x-ray light is diffracted in the x-direction.

Each active or passive subarea extends within the transverse surface in the x-direction in this case preferably across a whole number of diffraction strips. The transition between active and passive subareas of a lateral face therefore preferably coincides in each case with the transition between two diffraction strips. Active and passive subareas are in this case preferably arranged offset with respect to one another at the two lateral faces of a diffraction ridge. In a diffraction strip in which a first lateral face of each diffraction ridge has an active subarea, the other lateral face of the same diffraction ridge accordingly has a passive subarea, and vice versa. An exception to this rule is formed in this case by diffraction strips without diffraction effect in the x-direction (neutral diffraction strips), in which both lateral faces of a diffraction ridge each have passive subareas.

The passive subareas can be aligned exactly in the transverse surface parallel to the x-axis (g=0). Preferably, however, the passive subareas also have a small gradient (offset slope). Said offset slope is dimensioned in particular in such a way that the slope $\Delta y$ of the passive subareas caused thereby across one diffraction strip—measured in the y-direction—roughly corresponds to between 20% and 50%, preferably to roughly 25% of the strip width $s_L$ measured in the x-direction ($0.2 \leq \Delta y/s_L \leq 0.5$).

As a result of the offset slope of the passive subareas, at a given grating height and with given diffraction properties of the diffraction strips, the minimum distances between the sidewalls of the diffraction ridges—both within the diffraction ridges and between adjacent diffraction ridges—can advantageously be increased further.

In addition, the offset slope of the passive subareas brings about a flattening of the angles formed between the active and passive subareas, which is favorable in terms of the technical producibility of the lens grating $G_L$.

Since the offset slope in each case relates equally to the upper and lower material rim of a column, it does not change the phase shift encoded thereby. The offset slope causes a rectangle ("gradient 0") to become a parallelogram. The parallelogram has exactly the same effect as a rectangle on the phase of the light passing through. The offset slope is beneficially chosen as equal between upper rim and subjacent lower rim of the material. Different columns may also receive different additional gradients for rims which possess an x component (purely vertical jumps in the y-direction are not affected). A column in the left and in the right part (in the x-direction) can also possess a different offset slope if a break point is inserted therebetween.

In a beneficial embodiment variant of the lens grating $G_L$ each diffraction ridge extends diagonally within the transverse surface in alternating sections in the positive y-direction and in the negative y-direction. The diffraction ridges therefore have break points. The diffraction ridges preferably have oppositely arranged break points in alternation at regular intervals along the x-axis so that the respective diffraction ridge extends in meandering fashion within the transverse surface in the direction of the x-axis. The intermediate ridges made of photoresist, fashioned initially by exposure to x-radiation and developed subsequently, are mechanically stabilized during the manufacture of the lens grating $G_L$ using the LIGA method as a result of the single-break point or multi-break point layout for the diffraction ridges. The break points are preferably provided in each case in the vicinity of neutral or weakly diffracting diffraction strips. The course of each diffraction ridge within the transverse surface therefore changes direction in each case at diffraction strips having a small or vanishing diffraction effect.

Beneficially a uniformly predefined number of diffraction strips are always aligned in each case to a common focus. The diffraction strips aligned to a common focus are in this case referred to in summary as a focusing group. In this case the focusing groups preferably each comprise an uneven number of diffraction strips, e.g. 3, 5, 7 or 9 diffraction strips. Such a focusing group comprises a neutral diffraction strip having a vanishing diffraction effect around which the further diffraction strips of the focusing group are symmetrically arranged, their diffraction effect increasing in the x-direction with increasing distance from the neutral diffraction strip. The diffraction strips of adjacent focusing groups are in this case interleaved in one another.

Furthermore, one or more of the above-described embodiment features are provided in preferred embodiment variants of the lens grating $G_L$ in order to further increase the minimum distances within the diffraction ridges and between adjacent diffraction ridges and/or in order to optimize the optical properties of the lens grating $G_L$:

F1—"Gradient compression": This embodiment feature is applied in particular to the strongest subprisms (i.e. the active subareas of the diffraction ridges having the greatest gradients in each case) if at a given grating height h and given strip width $s_L$ of the diffraction strips a sufficiently strong diffraction cannot be achieved by means of an active subarea which extends linearly within the xz plane across the entire strip width $s_L$ and grating height h ($g=h/s_L$). The gradient compression is realized by the active subarea not being conducted across the full strip width $s_L$, but only across a portion $1/c$ (where $c>1$) of said strip width $s_L$, while the active subarea preferably extends across the entire grating height h in the z-direction. In this case the gradient g increases to $g=c \cdot h/s_L$. At the maximum visibility the gradient compression changes little at least when the intensity is relatively low in the remaining edge of the diffraction strip. If, for example, the high-intensity strips of the interference pattern formed by the phase grating $G_1$ in the diffraction grating $G_L$ fall exactly onto one strip, then the main intensity flows in the center of the strip (=slit center) and the edge remains comparatively dark. By means of the gradient increased by gradient compression it becomes possible to keep the distance between the patient and the x-ray detector comparatively small, which also improves the sensitivity. The smaller distance results in each diffraction strip being mapped onto a narrower region, thus improving the visibility for low compression (e.g. at $c^2<2$). At greater compression (e.g. $c^2>2$), on the other hand, the reduction in visibility predominates due to the edge losses in the most strongly diffracting subprisms. In a beneficial dimensioning, c is chosen in the range $4/3 \leq c \leq 3/2$, such as e.g. $c=2^{1/2}$. The gradient compression is preferably performed symmetrically with regard to the associated diffraction strip. The active subarea reduced in its width (in the x-direction) is therefore centered with respect to the associated diffraction strip.

Variant: A method described in application US 2012/0041679 A1 aims to align all the gratings in a computed tomography system based on phase-contrast imaging such that in the absence of the patient in the beam the bright strips of the interference pattern generated by the phase grating $G_1$ are aligned precisely onto the strip boundaries of the analysis grating. During a full revolution of the computed tomography system (in the absence of the patient) the strip is then shifted by the patient once to e.g. the right and (after a 180° gantry rotation) once in the opposite direction (in this case e.g. to the left). This can be sampled without any grating displacement and converted into images. Transferring this idea to the phase-contrast x-ray imaging device according to the invention, the gradient compression is beneficially performed asymmetrically. In this case it is beneficially specified in advance which slit boundaries of the lens grating $G_L$ are to receive the high intensity. The compressed gradient is shifted from the center of the strip to said slit boundary. The asymmetric compression therefore has the gradient-free part of the width $s_L(1-1/c)$ contiguously on the initially unilluminated side of the diffraction strip and the gradients up to the edge of the illuminated slit boundary.

F2—Gradient variation: With the lens gratings $G_L$ described in WO 2013/160153 A1, the subprisms or subareas are always aligned in such a way that all of the subprisms or subareas focus a design wavelength $\lambda_D$ or design photon energy as precisely as possible onto a common focus in which the center of the associated element of the analysis grating $G_2$ (slit or ridge) or of the detector pixel is placed. However, this restricts the layout more severely than necessary: Owing to dispersion, the strongest subprisms distribute the light intensity over a wide range (often over more than one pixel width or $S_2$ slit width). Their gradients are therefore not variable without further visibility losses in the associated diffraction strips. However, the weaker the subprisms become (the closer the subprisms lie to the associated focus along the x-axis, the closer to one another the individual wavelengths are mapped, the narrower therefore becomes the illuminated region overall. This affords the freedom to increase or reduce the gradient of said prisms slightly without significantly degrading the visibility. The weakest subprisms are generally located (along the x-axis) between the strongest subprisms and the second-strongest subprisms of the adjacent focusing group. In this case the minimum distances within the diffraction ridges and between the diffraction ridges can be increased by slight strengthening of said weakest subprisms by compressing the associated subareas in the z-direction. Often gradients of now equally strong neighboring subprisms can also be reduced, thus reducing the absorption by the lens grating $G_L$.

F3—Variation of the base height: The base height (i.e. the rectangular or parallelogram-shaped part of the material present across the full strip width in the layout) can be changed in order to improve the material aspect ratio. The aspect ratio is in this case reduced by increasing the base height through addition of material in the layout across the full strip width. Alternatively hereto, the free space aspect ratio can be improved by reducing the base height—this can also be utilized at a given and over-fulfilled aspect ratio in order to reduce the material fraction and consequently the absorption. This change mainly affects weak subprisms (having a small gradient) and medium-strength subprisms.

With weak subprisms it is advisable to use a gradient increase (see F2) for material-saving optimization of the aspect ratio, instead of increasing the base height, as long as visibility is not significantly reduced.

F4—Central column: In the lens gratings $G_L$ described in WO 2013/160153, the central (and optically neutral) diffraction strip of each focusing group is always completely filled with material. This necessitates a comparatively strong absorption in the central diffraction strips, where in actual fact nothing at all would be necessary for optical reasons (since no gradient at all needs to be realized in the central diffraction strips).

It is conceivable here to mirror the structure at the central column completely (i.e. structure axially symmetric to the y-axis in the middle of the central column) and for this purpose to incorporate rectangular material gaps across the full width of the central diffraction strips (or somewhat more or somewhat less). These gaps are neutral from the point of view of the diffraction, but reduce the absorption. They should be dimensioned such that they do not fall below minimum material widths. Preferably they correspond to a phase shift of the light passing through along the z-axis by an integral multiple of full wavelengths (analogously to F6 or F7, for a wavelength of the spectrum close to the design wavelength).

F5 "Gradient narrowing": This measure is very similar to the gradient compression described under point F1, but is applied, not to the strongest subprisms, but predominantly to the weakest subprisms. If their gradient is trimmed to fit in the strip-shaped layout at the outer and/or inner material edge in the direction of the strip center of the diffraction strip with strip width $s_L$, the minimum distances can be increased as a result.

If the outer edge is trimmed to fit (this being the edge in which little or no material is present in the y-direction), the meander-shaped material strip formed from two adjacent columns becomes narrower overall. The free space minimum distance can thus be increased. If the inner edge is trimmed to fit (this being the edge in which a lot of material is present in the y-direction), the column boundary between the adjacent diffraction strips of the meander-shaped material strip is finally shifted in the direction of the weaker subprism. The material minimum distance can be increased in this way. In this case a maximum of 10-15% of the strip width should be affected (in order to have little impact on the maximum visibility).

F6—Dispersion correction: An increase in the geometric gradient of the strongest subprisms is achieved by means of the gradient compression explained under point F1. That said, however, the light deflection of the diffraction strips does not increase to the same extent. This effect can be employed for dispersion correction in the case of the strongest subprisms. Since the refractive index is $\delta \propto \lambda^2 \propto 1/E^2$ and the deflection angle $\gamma \approx \delta \times g$, it follows that $\gamma$ is $\propto \lambda^2 \propto 1/E^2$. Let there be given a strong gradient which increases the material height (and consequently the phase due to the higher phase velocity through the material) in the direction of the positive x-axis (and consequently deflects the light in the negative x-direction). Let the x distance Lx now be chosen to match the gradient g such that it holds that $\Delta\Phi=2\pi$ $(\delta/\lambda)g\,\Delta x=2\pi$, i.e. that along $\Delta x$ the phase changes due to the gradient by precisely $\Delta\Phi=2\pi$ or, as the case may be, the wavefront is displaced by $\Delta z=+\lambda_D$ in the propagation direction (for a design wavelength $+\lambda_D$ preferably lying close to the center of the dimensioning spectrum). If, in this case, in the positive x-direction of the increasing material height, the material height is now reduced abruptly by $\Delta h=g\cdot\Delta x$ such that a phase jump of $\Delta\Phi=-2\pi$ or $\Delta z=-\lambda_D$ results, this is without any impact for the design wavelength $\lambda_D$ (since only the phase modulo $2\pi$ is relevant). For a wavelength $\lambda=f\cdot\lambda_D$ changed by a factor f, however, $\delta(\lambda)/\lambda\propto f\cdot\lambda_D$ applies, so that due to $\Delta\Phi=2\pi\,(\delta/\lambda)\Delta h$ a phase deviation of $2\pi\cdot(1-f)$ remains locally at the jump point. If deviations of $\pm\pi/4$ are tolerated, then $3/4\leq f\leq 5/4$ must therefore apply. The spectrum therefore has a bandwidth of the factor $5/3=167\%$ (which fits well with regard to the previous bandwidth of the lens grating $G_L$ of the factor $3^{1/2}$ 173%). If a phase jump opposite to the gradient is generated every Lx (as a result of which the material height describes a sawtooth curve without any central slope), however, the phase deviation $2\pi$ due to the gradient is compensated with that due to the phase jump, with the result that on average the phase (except for the local deviation of $2\pi\cdot(1-f)$) can be approximated by the straight line $\Delta\Phi=2\pi\cdot x/\Delta x$, and moreover irrespective of f or $\lambda$. For the x-radiation, it therefore appears like an errored continuous slope at $\delta\propto\lambda^1\propto 1/E^1$. Deflection angles linear to f: $\gamma\propto\lambda^1\propto 1/E^1\propto f$ result. The color error can therefore be reduced in this way by an order of magnitude. If a phase jump is inserted at shorter intervals than $\Delta x$, there may possibly be an overcompensation, which may be beneficial to a limited extent. The use of phase jumps is advisable only in order to correct color errors if $(\delta/\lambda)g\cdot s_L$ is greater than or at least not significantly less than 1.

Numeric examples: For E=62 keV photons, a full phase jump corresponds to a gold height of h=25 μm (transmission 85%) or a nickel height of 43 μm (transmission 95%). At E=29 keV, on the other hand, it is a nickel height of 20 μm (transmission 82%) or a silicon height of 75 μm (transmission 98%). At E=19 keV photons, the jump by a phase corresponds to a silicon height of 50 μm (transmission 95%).

A problem with this strategy is that enough material must remain at the jump point to fulfill the minimum widths of the layout. For this reason the negative phase jump saves material on the one hand, though on the other hand material must also be added so that there is still enough material at the jump points. Ultimately this may mean that material has to be added.

F7—Additional phase jumps: In contrast to the dispersion correction discussed under point F6, in this case the dispersion is increased (and at small gradients is then approximately independent of a variation of the gradient). Beneficially, the dispersion of the weakest subprisms is increased by means of one or more additional $2\pi$ jumps (jumps by one wavelength in each case). This causes the material fraction in the layout to increase initially, and as a result the material minimum distance can—as desired—also increase. This measure does, however, permit the base height discussed under point F3 to be reduced and consequently the free space minimum distance to be reduced. Finally the material/free space boundary in the strip of the weakest subprisms accordingly approaches the material/free space boundary of the oppositely disposed strongest subprisms in rough approximation. Through the choice of the x positions of the $\lambda$ phase jumps within the strip it is possible to influence whether the free space distance (in the direction of the oppositely disposed strongest subprisms) is to be influenced more strongly or less strongly than the material distance (within the meander-shaped material strip with the adjacent prism column). At greater grating heights it may also make sense to distribute a plurality of complete phase jumps relatively uniformly over the column width (e.g. three phase jumps at the positions 12.5%, 50%, 87.5% of the subprism width or at the x positions 25%, 50%, 75% of $s_L$). This also applies analogously to the dispersion correction discussed under point F6.

The embodiment features of the diffraction ridges and of the active subareas (subprisms) contained therein discussed under points F1 to F6 can advantageously be used both for diagonal layouts of the diffraction ridges and for strip-shaped layouts according to WO 2013/160153 A1 in order to further increase the minimum distances within the diffraction ridges and between adjacent diffraction ridges and/or to optimize the optical properties of the lens grating $G_L$. Each of the features discussed under points F1 to F6 is therefore considered also per se (irrespective of the large-scale course of the diffraction ridges in the transverse surface) as an independent invention.

As described hereintofore, in a lens grating $G_L$ a uniformly predefined number of diffraction strips are in each case aligned onto a common focus, the diffraction strips aligned onto a common focus being referred to in summary as a focusing group. Such a focusing group comprises a neutral diffraction strip with vanishing diffraction effect around which further diffraction strips of the focusing group are symmetrically arranged, their diffraction effect increasing in the x-direction with increasing distance from the neutral diffraction strip. In the case of the diffraction gratings $G_A$ and/or $G_B$, on the other hand, the successive diffraction strips diffract alternately to the left and to the right, i.e. in the direction of the positive or the negative x-axis, and the diffraction effect of diffraction strips succeeding one another in the direction of the x-axis changes only in alternation between two adjacent diffraction strips. Accordingly, in the case of a diffraction grating $G_A$ and/or $G_B$ a plurality of diffraction strips are not aligned onto a common focus and accordingly different diffraction powers are also not realized for different diffraction strips. It could effectively be said that the diffraction gratings $G_A$ and $G_B$ represent a limiting case of the lens grating $G_L$ in which each focusing group is given by a single diffraction strip.

As already presented in detail, the phase-contrast differential amplifier serves to increase the sensitivity of the phase-contrast x-ray imaging device. In contrast, a previously described lens grating $G_L$ is used in order to increase the visibility, as is described in WO 2013/160 153 A1. According to an advantageous embodiment variant of the phase-contrast x-ray imaging device, the two principles are combined with one another and accordingly the phase-contrast x-ray imaging device in this case has a phase-contrast differential amplifier and furthermore an additional diffraction grating embodied in the manner of a previously described lens grating $G_L$ is arranged between the phase-contrast differential amplifier and the x-ray detector.

BRIEF DESCRIPTION OF THE SEVERAL VIEWS OF THE DRAWING

Exemplary embodiments of the invention are explained in more detail below with reference to a schematic drawing, in which:

FIG. 7 shows a second alternative embodiment of the phase-contrast differential amplifier in a schematic view, FIG. 8 shows a third alternative embodiment of the phase-contrast differential amplifier in a schematic view.

Mutually corresponding parts are in each case labeled with the same reference signs in all of the figures.

DESCRIPTION OF THE INVENTION

Figure 1:
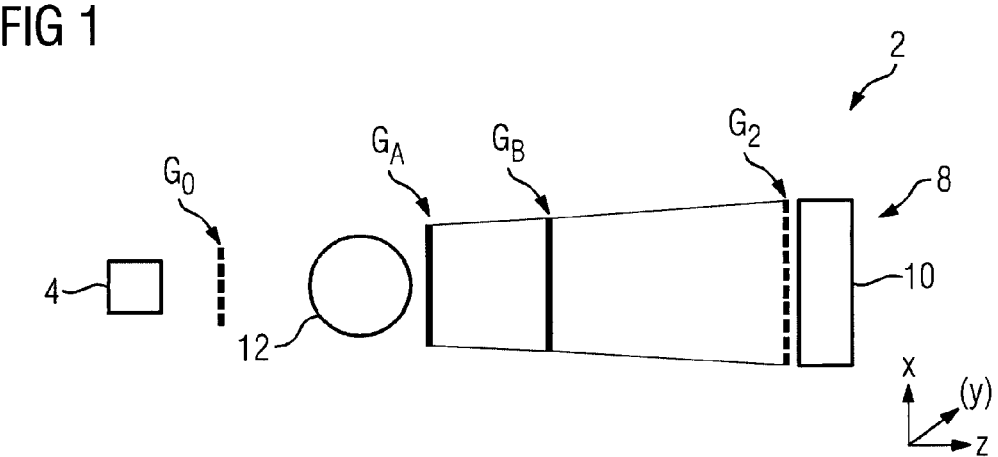
FIG. 1 shows a phase-contrast x-ray imaging device in a schematic view.

A phase-contrast x-ray imaging device 2 described by way of example below and outlined in FIG. 1 comprises, exactly like a conventional Talbot-Lau interferometer 4 shown schematically in FIG. 2, an x-ray tube 6, a coherence grating $G_0$, an analysis grating $G_2$, and an x-ray detector 8 having a regular arrangement of detector pixels 10 which are arranged along a z-axis. Additionally positioned between the x-ray tube 6 serving as x-ray source and the x-ray detector 8 is a patient couch 12 which serves as a support for a patient that is to be examined by means of the phase-contrast x-ray imaging device 2 and consequently by means of phase-contrast imaging.

As is evident from FIG. 1, the phase grating $G_1$ of the conventional Talbot-Lau interferometer 4 is replaced in the phase-contrast x-ray imaging device 2 by two diffraction gratings $G_A$ and $G_B$ which together embody a phase-contrast differential amplifier 14.

Figure 3:
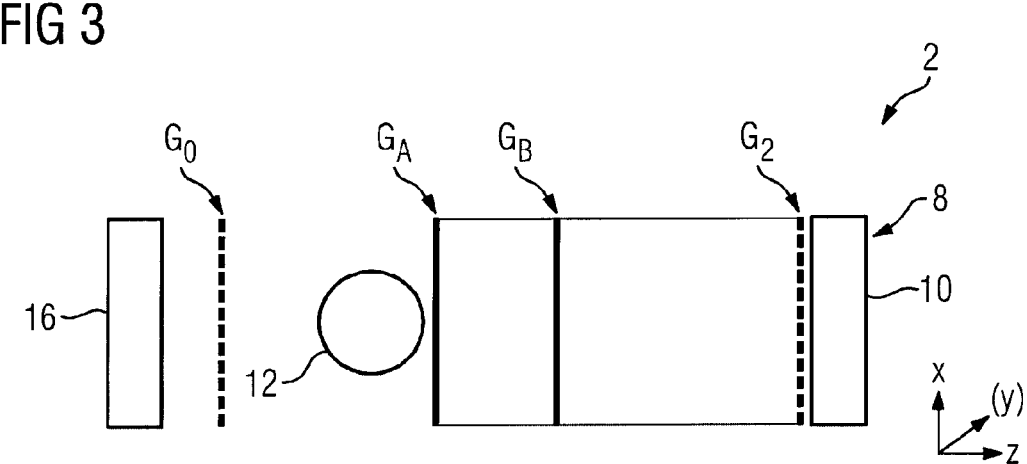
FIG. 3 shows an alternative embodiment of the phase-contrast x-ray imaging device in a schematic view.
Figure 4:
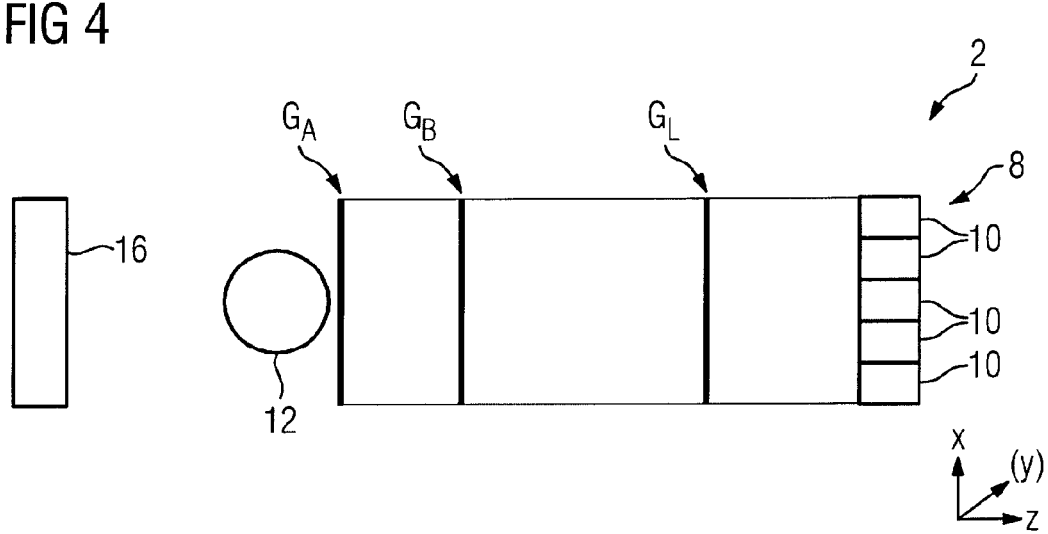
FIG. 4 shows a second alternative embodiment of the phase-contrast x-ray imaging device in a schematic view.

The layout of the phase-contrast x-ray imaging device 2 outlined in FIG. 1 can be varied in this case for different application purposes and two alternative layouts are indicated in FIG. 3 and FIG. 4. In both cases a synchrotron radiation source 16 serves as an x-ray source instead of the x-ray tube 6, wherein in the case of the embodiment variant according to FIG. 4 a synchrotron radiation source 16 is provided which to a very good approximation generates x-radiation having plane wavefronts, such that with this layout a coherence grating $G_0$ can be dispensed with. Furthermore, the analysis grating $G_2$ is replaced in this layout by a lens grating $G_L$, as is known from WO 2013/160 153 A1.

If, on the other hand, a coherence grating $G_0$ having the period $p_0$ is used, then in this case essentially only every 2N-th slit may be open, where N is the number of strips of width $s_B$ at the z position along the z-axis of $G_B$, such that the electromagnetic radiation entering in strips of width $s_A$ at the z position of $G_A$ is shifted until it exits at $G_B$. Compared with a conventional Talbot-Lau interferometer, the period $p_0$ is in this case shortened by the same factor 2N. The reason for this is that the contrast or the intensity increases and decreases more quickly by this factor (if $G_0$ is shifted or rotated in the direction of the incoming beam) compared with the conventional Talbot-Lau interferometer. If a plurality of adjacent slits are open, this makes itself increasingly noticeable as interference in respect of the sensitivity of the Talbot effect between $G_B$ and $G_2$. This problem is already described in a somewhat different context in WO 2013/160 153 A1.

Figure 2:
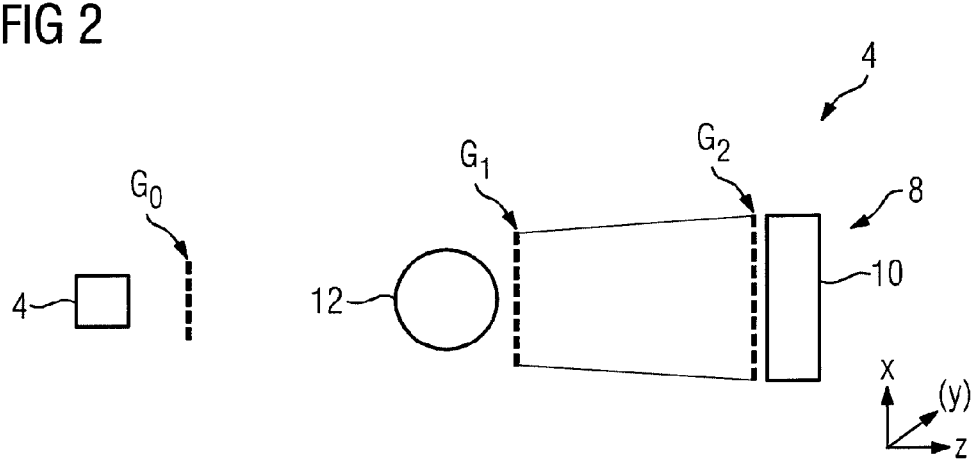
FIG. 2 shows a conventional Talbot-Lau interferometer in a schematic view.

According to a further embodiment variant, not described in greater detail, the two layouts from FIG. 1 and FIG. 2 are realized in a common imaging device, i.e. a computed tomography system, for example, and in that case are utilized in turn. Accordingly, a measurement is then carried out using the layout with phase-contrast differential amplifier 14 in order to register small phase changes at low visibility but high sensitivity (in the case of greater phase changes, phase wrapping occurs and the measurement error may not be noticed) and in parallel or slightly offset in time with respect hereto an additional measurement is carried out with the layout without phase-contrast differential amplifier 14 in order to measure greater phase changes correctly at reduced sensitivity but higher visibility (in the case of smaller phase changes, this measurement method is subject to higher noise on account of the lower sensitivity and is therefore less suitable).

To that end the two layouts are installed, for example offset by 90° relative to one another, e.g. in a computed tomography system (in this case the entire x-ray dose for each measurement can be distributed freely over both measurement methods). Alternatively, the two layouts can also be merged with one another, wherein for example the detector region of the computed tomography system is subdivided in a direction parallel to the spinal column of a patient into a band for one measurement and a band for the other measurement (if the table feed-forward rate of the patient tables is reduced accordingly and more revolutions per feed-forward increment are permitted). This variant is suitable in particular when measurements are carried out without phase stepping.

The phase-contrast differential amplifier 14 employed in the phase-contrast x-ray imaging device 2 is built from two diffraction gratings $G_A$ and $G_B$ of similar type and serves to amplify local phase differences caused by an examination object, i.e. by a patient, and consequently for increasing the resolution capacity of the phase-contrast x-ray imaging device 2. The underlying functional principle can be illustrated in this case with reference to the schematic diagram shown in FIG. 5.

In this case a type of basic unit of the phase-contrast differential amplifier 14 is shown onto which there is incident from the left an unaffected wavefront 18 in one instance and a wavefront 20 affected by the patient in another instance, the direction of which wavefront 20 can be described by means of a non-zero phase gradient. If different beam paths a to h through the phase-contrast differential amplifier 14 are now considered, it is evident that in the case of the unaffected wavefront 18 the sum of the two paths traveled through the diffracting material of the two diffraction gratings $G_A$ and $G_B$ is independent of the x position at which the beam is incident on the diffraction grating $G_A$, with the result that a uniform phase shift takes place in this case.

In this case the sum of the two partial paths through the diffracting material at $G_A$ on the one side and at $G_B$ on the other side is always to be considered. The path traveled through the diffracting material of a single diffraction grating, i.e. either $G_A$ or $G_B$, on the other hand, varies without question as a function of the x position. However, these differences are evened out again through the combination of the two diffraction gratings $G_A$ and $G_B$, i.e. if the path traveled through the diffracting material of a beam path turns out to be smaller at the diffraction grating $G_A$, then the path traveled through the diffracting material at the diffraction grating $G_B$ is correspondingly greater, and vice versa, as is shown by the comparison of the beam paths a or h and d or e.

If, on the other hand, the wavefront is incident on the diffraction grating $G_A$ at a specific angle, as in the case of the affected wavefront 20, then the path traveled through the diffracting material changes as a function of the x position. Thus, in the case of the beam path c the entire material height during the passage through the diffraction grating $G_A$ and through the grating $G_B$ is reduced, and in the case of the beam path g is increased, as a result of which the phase gradient given at the input of the phase-contrast differential amplifier 14 is amplified during the passage through the phase-contrast differential amplifier 14. There is therefore to all intents and purposes a phase shift due to different path lengths through the diffracting material.

Based on this effect, a phase-contrast differential amplifier 14 can now be realized which is built from two diffraction gratings $G_A$ and $G_B$ that have a regular structure formed from diffracting material by means of which quasi-diffracting prisms are realized which diffract alternately in the direction of an x-axis and in the opposite direction to the x-axis when wavefronts are incident at a specific angle on the diffraction grating $G_A$ and $G_B$, in other words when a beam does not enter perpendicularly to the surface.

Corresponding regular structures are indicated in the schematic diagrams in FIG. 6 to FIG. 9. The figures in this case depict outlines compressed to different degrees of intensity in the direction of the x-axis, i.e. the x-axis ought actually to be stretched strongly with respect to the diagram. In this case different prism strengths, i.e. different gradients of the inclined rims, are shown in the diagrams, the prism strength of a diffraction grating preferably always being dimensioned such that the strip-shaped interference pattern is shifted by the phase-contrast differential amplifier 14 by an integral number N of strips or an integral multiple N of the strip width.

The displacement in this case also causes a phase shift by the gradient along N strips, such that adjacent partial beams i, j exiting at the diffraction grating $G_B$ exhibit 2N times the phase shift compared to the phase shift of said partial beams at the input of the phase-contrast differential amplifier 14. This is a further effect in which a phase jump is given due to the displacement of the interference pattern.

Figure 5:
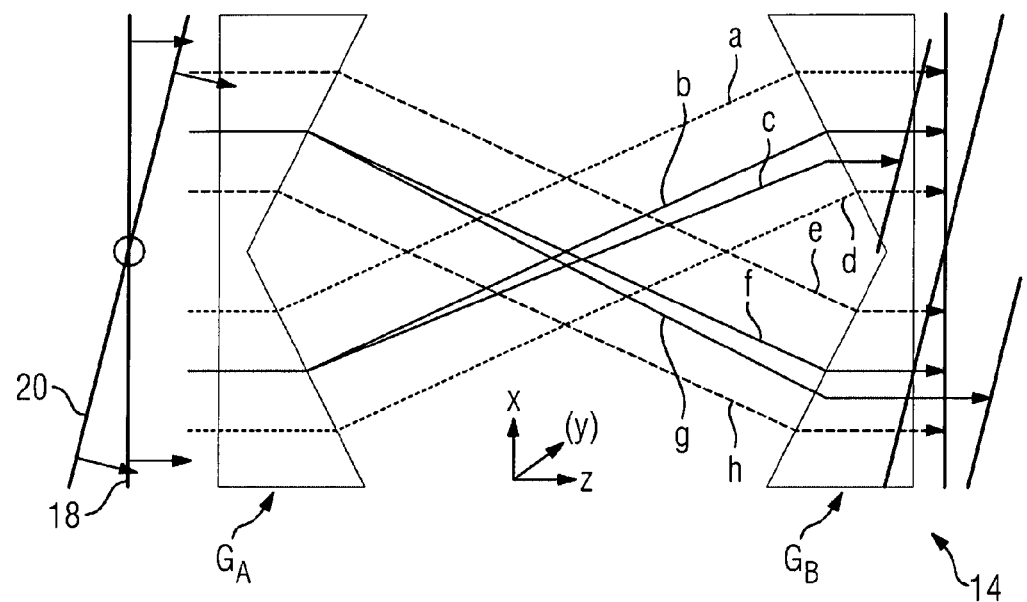
FIG. 5 shows a phase-contrast differential amplifier in a detail view.
Figure 6:
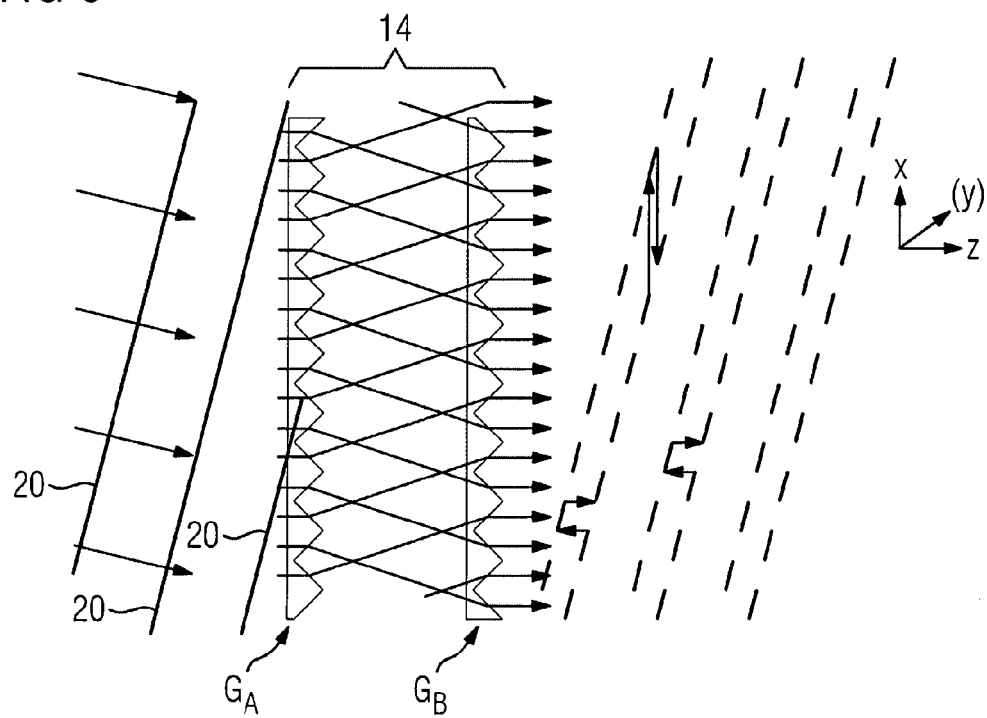
FIG. 6 shows an alternative embodiment of the phase-contrast differential amplifier in a schematic view.
Figure 9:
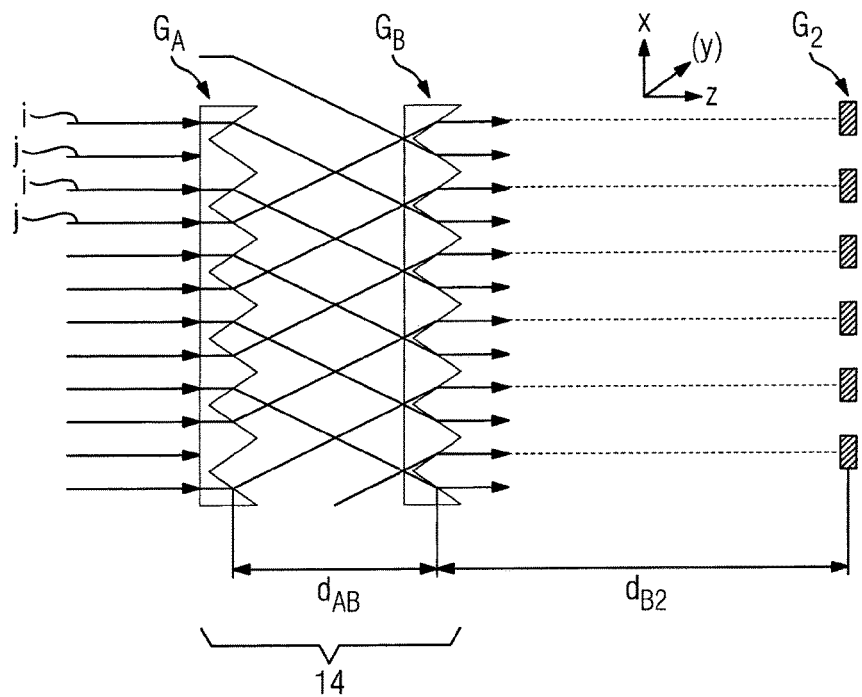
FIG. 9 shows a fourth alternative embodiment of the phase-contrast differential amplifier in a schematic view.

However, this additional effect is compensated by a further effect of approximately the same strength, which can be understood with the aid of the illustration shown in FIG. 5. Comparing the beam paths b and c as well as f and g, it is apparent that, depending on beam path, the electromagnetic radiation has to negotiate different travel paths along an x-axis perpendicular to the z-axis, which likewise influences the phase of the electromagnetic radiation. By means of corresponding calculations it can be demonstrated that all three effects have roughly the same strength, so that, as it were, two effects cancel one another out.

Figure 10:
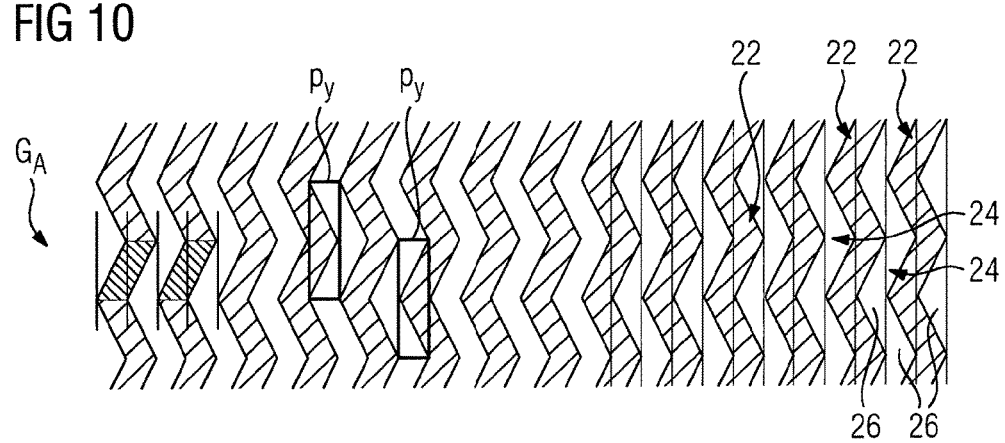
FIG. 10 shows a layout for producing a phase-contrast differential amplifier in a schematic view.
Figure 11:
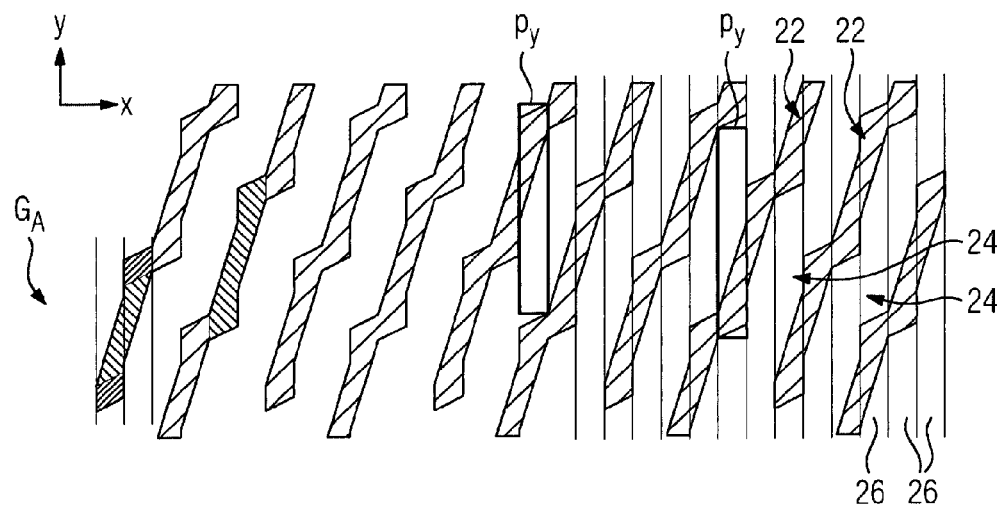
FIG. 11 shows an alternative layout for producing a phase-contrast differential amplifier in a schematic view.
Figure 12:
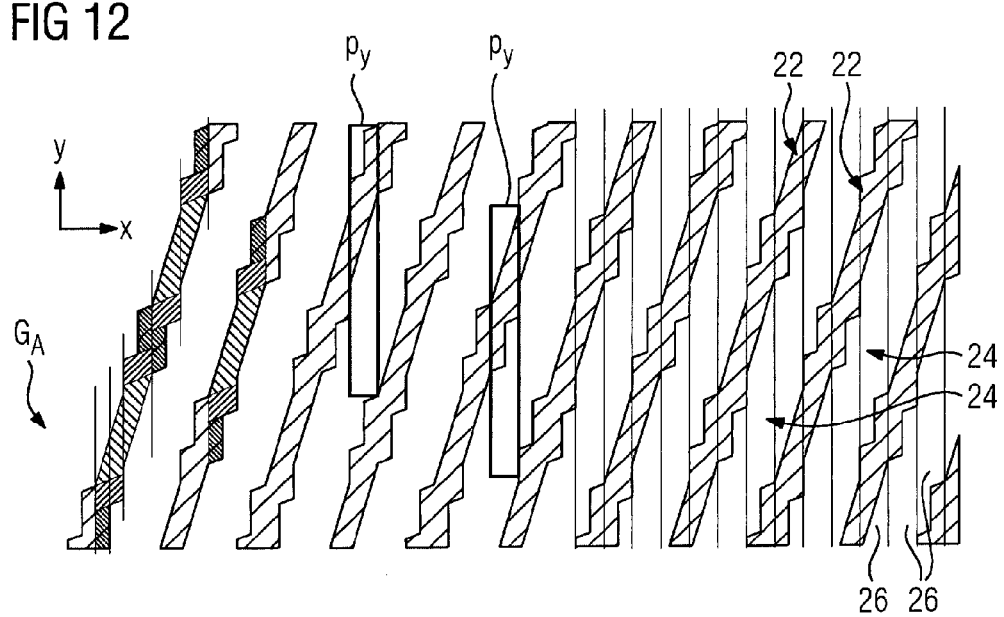
FIG. 12 shows a second alternative layout for producing a phase-contrast differential amplifier in a schematic view.

The required structures for the diffraction gratings $G_A$ and $G_B$ can be implemented for example by means of off-axis illuminated photolithography and layouts suitable for this purpose are depicted in the schematic diagrams in FIG. 10 to FIG. 12. Shown here in each case is the end face or grating plane of a diffraction grating $G_A$ or $G_B$ at right angles to the z-axis which extends in the direction of the x-axis and in the direction of a y-axis perpendicular thereto.

The layouts in this case show different embodiments of diffraction ridges 22 by means of which incident electromagnetic radiation experiences a phase shift, the diffraction ridges 22 being separated from one another by interspaces 24 through which electromagnetic radiation can pass substantially without a phase shift. A diffraction grating $G_A$ or $G_B$ is then realized with the aid of the diffraction ridges 22, in which diffraction grating $G_A$ or $G_B$ x-radiation is diffracted to the left and to the right in turn, i.e. alternately, in succeeding diffraction strips 26, i.e. in the direction of the x-axis and in the opposite direction to the x-axis, respectively.

The invention is not limited to the exemplary embodiment described hereinabove. Rather, other variants of the invention can also be derived herefrom by the person skilled in the art without departing from the subject matter of the invention. In particular it is furthermore possible also to combine all the individual features described in connection with the exemplary embodiment with one another in other ways without departing from the subject matter of the invention.

| List of reference signs | |
|---|---|
| 2 | Phase-contrast x-ray imaging device |
| 4 | Talbot-Lau interferometer |
| 6 | X-ray tube |
| 8 | X-ray detector |
| 10 | Detector pixel |
| 12 | Patient couch |
| 14 | Phase-contrast differential amplifier |
| 16 | Synchrotron radiation source |
| 18 | Unaffected wavefront |
| 20 | Affected wavefront |
| 22 | Diffraction ridge |
| 24 | Interspace |
| 26 | Diffraction strip |
| $G_0$ | Coherence grating |
| $G_1$ | Phase grating |
| $G_2$ | Analysis grating |
| $G_A$ | Diffraction grating |
| $G_B$ | Diffraction grating |
| $G_L$ | Lens grating |
| $P_x$ | Grating period of the grating $G_x$ |
| $P_y$ | Period length of a diffraction grating along the y-axis |
| $D_{xy}$ | Distance between the gratings $G_x$ and $G_y$ |
| a . . . h | Beam path |
| i | Partial ray |
| j | Partial ray |
| x | x-axis |
| y | y-axis |
| z | z-axis |

The invention claimed is:

1. A phase-contrast x-ray imaging device, comprising:
an x-ray source for generating an x-radiation field;
an x-ray detector having a one-dimensional or two-dimensional arrangement of pixels; and
a phase-contrast differential amplifier disposed between said x-ray source and said x-ray detector and configured to amplify spatial phase differences in the x-radiation field during operation;
said phase-contrast differential amplifier having two diffraction gratings which, when viewed in a radiation incidence direction, are arranged one behind another; and wherein each said diffraction grating includes:
a transverse surface to be aligned substantially at right angles to the radiation incidence direction and being spanned by an x-axis and a y-axis perpendicular thereto; and a plurality of diffraction ridges made of an optically comparatively thin base material arranged in alternation with optically denser interspaces;

said diffraction ridges being formed to subdivide the transverse surface into elongate diffraction strips that extend in each case in a y-direction and that are arranged next to one another in parallel rows in an x-direction, wherein adjacent diffraction strips are different from one another in that they are always aligned to different focuses in terms of the diffraction properties of a grating material arranged in each case in a vicinity of said diffraction strip or diffract in different directions.

2. The phase-contrast x-ray imaging device according to claim 1, wherein said phase-contrast differential amplifier is configured such that unaffected x-radiation experiences a uniform phase shift due to said phase-contrast differential amplifier irrespective of an entry position of the unaffected x-radiation at said phase-contrast differential amplifier.

3. The phase-contrast x-ray imaging device according to claim 1, wherein said two diffraction gratings of said phase-contrast differential amplifier are two identical diffraction gratings.

4. The phase-contrast x-ray imaging device according to claim 1, wherein said diffraction ridges are formed to extend diagonally at least in sections within the transverse surface, wherein lateral faces of at least one said diffraction ridge which delimit said diffraction ridge in the x-direction in each case extend across a plurality of said diffraction strips.

5. The phase-contrast x-ray imaging device according to claim 1, wherein said diffraction ridges are formed as oblique prisms inclined in the y-direction, and having a base surface and a top surface that lie in the end faces of said diffraction grating that are parallel to the transverse surface.

6. The phase-contrast x-ray imaging device according to claim 5, wherein:

said diffraction ridges are arranged such that in each diffraction strip there results a material structure repeating itself with a y-period length in the y-direction; and said diffraction ridges are inclined in the y-direction such that a top surface of each diffraction ridge opposite the base surface is offset with respect to the base surface by a whole number of period lengths.

7. The phase-contrast x-ray imaging device according to claim 6, wherein the top surface of each diffraction ridge opposite the base surface is offset with respect to the base surface by precisely one period length.

8. The phase-contrast x-ray imaging device according to claim 1, wherein each said diffraction ridge adjoins the interspaces arranged between said diffraction ridges with two lateral faces in each case, wherein said lateral faces are composed of active subareas having a comparatively strong diffraction effect in the x-direction alternating with passive subareas having a small or neglectable diffraction effect in the x-direction.

9. The phase-contrast x-ray imaging device according to claim 8, wherein each active or passive subarea extends across a whole number of diffraction strips in the x-direction.

10. The phase-contrast x-ray imaging device according to claim 1, which comprises an object support for accommodating an examination object disposed between said x-ray source and said phase-contrast differential amplifier.

11. The phase-contrast x-ray imaging device according to claim 1, which further comprises an analysis grating arranged between said phase-contrast differential amplifier and said x-ray detector.

12. The phase-contrast x-ray imaging device according to claim 1, which further comprises a coherence grating arranged between said x-ray source and said phase-contrast differential amplifier.

13. The phase-contrast x-ray imaging device according to claim 1, which further comprises an additional diffraction grating arranged between said phase-contrast differential amplifier and said x-ray detector.

* * * * *